United States Patent [19]

Kane

[11] Patent Number: 5,037,615

[45] Date of Patent: Aug. 6, 1991

[54] TETHERED PAIR FLUORESCENCE ENERGY TRANSFER INDICATORS, CHEMICAL SENSORS, AND METHOD OF MAKING SUCH SENSORS

[75] Inventor: James A. Kane, Miami, Fla.

[73] Assignee: Cordis Corporation, Miami, Fla.

[21] Appl. No.: 115,153

[22] Filed: Oct. 30, 1987

[51] Int. Cl.$^5$ .................... G01N 21/64; G01N 21/77
[52] U.S. Cl. ............................... 422/82.08; 128/634; 250/483.1; 422/57; 422/58; 422/82.07; 422/82.11; 436/172
[58] Field of Search .................. 436/172.89; 422/55, 422/56, 57, 58, 82.07, 82.08, 82.11; 128/634; 250/459.1, 461.1, 483.1

[56] References Cited

U.S. PATENT DOCUMENTS

| | | | |
|---|---|---|---|
| Re. 32,475 | 8/1987 | Nishida et al. | |
| 4,200,110 | 4/1980 | Peterson et al. | |
| 4,476,870 | 10/1984 | Peterson et al. | |
| 4,495,293 | 1/1985 | Shaffar | |
| 4,507,230 | 3/1985 | Tam et al. | |
| 4,577,109 | 3/1986 | Hirshfeld | |
| 4,610,966 | 9/1986 | Fuchs | 436/89 X |
| 4,682,895 | 7/1987 | Costello | |
| 4,743,561 | 5/1988 | Shaffar | 436/172 X |
| 4,929,561 | 5/1990 | Hirschfeld | 422/82.06 |

FOREIGN PATENT DOCUMENTS

| | | |
|---|---|---|
| 73558 | 3/1983 | European Pat. Off. |
| 205232 | 12/1986 | European Pat. Off. |

OTHER PUBLICATIONS

Merrifield, "Solid Phase Peptide Synthesis. I. The Synthesis of a Tetrapeptide", *Journal American Chemical Society*, vol. 85, pp. 2149–2154, Jul. 20, 1963.

Merrifield, "Solid Phase Peptide Synthesis. III. An Improved Synthesis of Bradykinin", *Biochemistry*, vol. 3, No. 9, Sep. 1964.

Stryer and Haugland, "Energy Transfer: A Spectroscopic Ruler", *Proc. National Academy of Science*, vol. 58, pp. 719–726, 1967.

Seitz, "Chemical Sensors Based on Fiber Optics", *Analytical Chemistry*, vol. 56, No. 1, Jan., 1984.

Jordan and Walt, "Physiological pH Fiber-Optic Chemical Sensor Based on Energy Transfer", *Analytic Chemistry*, vol. 59, pp. 437–439, 1987.

*Primary Examiner*—Robert J. Hill, Jr.
*Attorney, Agent, or Firm*—Lockwood, Alex, Fitzgibbon & Cummings

[57] ABSTRACT

A fluorescence energy transfer indicator, a chemical sensor incorporating it, and a method for making it are provided, such being useful in medical, biological and industrial applications. The fluorescence energy transfer indicator includes a rigid spacer group that tethers together a fluorescent energy donor and a colorimetric indicator acceptor, the tethering being across a predetermined, known or determinable length in order to thereby tailor the indicator to the specific needs of the chemical sensor. The emission spectrum of the fluorescent energy donor overlaps with an absorbance spectrum of the colorimetric indicator acceptor, which undergoes a change in color or in color intensity as a function of the species being monitored or measured in accordance with parameters of the species such as pH, oxygen concentration, carbon dioxide concentration and the like.

14 Claims, 1 Drawing Sheet

TETHERED PAIR FLUORESCENCE ENERGY TRANSFER INDICATORS, CHEMICAL SENSORS, AND METHOD OF MAKING SUCH SENSORS

BACKGROUND AND DESCRIPTION OF THE INVENTION

The present invention generally relates to energy transfer indicators for chemical sensors used in monitoring, detecting and/or measuring parameters at locations remote from detection instrumentation. More particularly, the invention relates to chemical sensor components that incorporate tethered pair fluorescence energy transfer indicators which are suitable for being positioned at a remote or distal portion of an optical fiber waveguide. These chemical sensor components incorporate a spacer of a known or a determinable length that tethers together a colorimetric indicator or acceptor and a fluorescent energy donor, and the absorbance spectrum of the colorimetric indicator overlaps with the emission spectrum of the fluorescent donor.

Fiber optical chemical sensors are generally known to be useful for a wide variety of purposes, especially in the areas of medicine, scientific research, industrial applications, and the like. Descriptive materials that discuss the structure, properties, functions and operational details of fiber optic chemical sensors include Hirschfeld U.S. Pat. No. 4,577,109 and Sietz, "Chemical Sensors Based on Fiber Optics", *Analytical Chemistry*, Vol. 56, No. 1, January, 1984, each of which is incorporated by reference hereinto. From publications such as these, it is known to incorporate a chemical sensor into a fiber optic waveguide in a manner such that the chemical sensor will interact with an analyte. The chemical sensor composition and analyte interaction results in a change in optical properties, which change is probed and detected through the fiber optic waveguide. These optical properties of the chemical sensor compositions typically involve changes in colors or in color intensities. In these types of systems, it is possible to detect particularly minute changes in the parameter being monitored in order to thereby provide especially sensitive monitoring capabilities.

A specific application of this fiber optic chemical sensor technology is found in Peterson et al U.S. Pat. No. 4,200,110, which shows a fiber optic pH probe. This patent is incorporated by reference hereinto. Other parameters that are typically suitable for measurement by fiber optic chemical sensors include oxygen concentrations and carbon dioxide concentrations which, together with pH, are typical blood parameters that need to be monitored in vivo. Fiber optic chemical sensors can also be used to detect metal ions such as $Al^{+++}$ and $Be^{++}$ and other metal ions that can be determined fluorometrically when in solution, including $Mg^{++}$, $Zn^{++}$ and $Cd^{++}$. Other uses for these types of devices include detection of biological fluids, glucose, ammonia, $UO^{++}$ and halides, the detection of which may require that reagents be diffused into the sample. Other areas in which fiber optic chemical sensors may be useful include the monitoring of chemical conditions during industrial processes, such as for taking industrial biological measurements. An example of a specific industrial type of application could include the use of long-length optical fibers in order to measure conditions within submerged wells or the like.

A typical approach in the construction of fiber optic chemical sensors requires the positioning of a dye material or other chemical indicator at a generally distal location with the assistance of various different support means. The support means must be such as to permit interaction between the dye material and the substance being subjected to monitoring, measurement and/or detection. Exemplary means include permeable membranes, microencapsulation, and the use of a gel-like support. Chemical indicators for such chemical sensors and the like include sensors that are based on the absorbance of dye materials which are covalently bound to polymer materials. An example is found in the Sietz article "Chemical Sensors Based on Fiber Optics", supra.

Proposals have been made, for example in connection with assay kits that do not incorporate fiber optics, to utilize energy transfer techniques in order to achieve fluorometric determinations. An example of such an approach is found in Shaffar U.S. Pat. No. 4,495,293. Such an approach provides an assay solution that includes a fluorescer and a reagent system which is capable of providing a change in the transmittive properties of the assay solution. An objective here is the development of fluorescence energy transfer, which is the transfer of the excited state energy from the donor to an acceptor. Assay solutions utilizing this general technique are limited in their ability to be tailored in order to respond to analytes of various specific values.

By proceeding in accordance with the present invention, it has been found that the phenomenon of fluorescence energy transfer can serve as a new class of indicators for chemical sensors. These can be described as molecules whose fluorescent output follows a characteristic response allowing, for example in the case of an optrode, for single point calibration. This approach for these types of chemical sensors also provides the ability to tailor the molecule to respond, for example, at any pH by simply selecting an appropriate indicator at the desired pH value.

In summary, the present invention relates to chemical sensor components that incorporate a spacer of a known or a determinable length which tethers or binds a fluorescent, environmentally insensitive molecule to a colorimetric or other fluorometric indicator. This spacer group is substantially rigid. The extent to which the fluorescent moiety emits is dependent upon the status of the colorimetric indicator, which is in turn dependent upon the species for which it is sensitive. The absorbance spectrum of the colorimetric indicator or acceptor overlaps with the emission spectrum of the fluorescent energy donor.

It is a general object of the present invention to provide an improved indicator for a chemical sensor, such as a fiber optic chemical sensor.

Another object of this invention is to provide an improved chemical sensor that utilizes fluorescence energy transfer between a tethered pair of moieties.

Another object of the present invention is to provide an improved chemical sensor that provides a fixed distance for fluorescence energy transfer from a fluorescent donor to a colorimetric indicator.

Another object of the present invention is to provide an improved chemical sensor suitable for devices incorporating fiber optics, which sensor incorporates fluorescence energy transfer between a tethered pair of moieties wherein the degree of energy transfer is dependent only on the extent of overlap of the emission spectrum of the fluorescent component with the absorbtion spectrum of the indicator component.

These and other objects, features and advantages of this invention will be clearly understood through a consideration of the following detailed description.

BRIEF DESCRIPTION OF THE DRAWINGS

In the course of this description, reference will be made to the attached drawings, wherein.

DESCRIPTION OF THE PARTICULAR EMBODIMENTS

Figure 1:
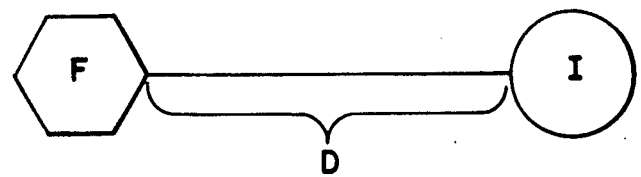
FIG. 1 is a schematic illustration of a tethered pair fluorescence transfer indicator that is incorporated into a chemical sensor according to this invention.

The tethered pair fluorescence energy transfer indicators for chemical sensors that are schematically illustrated in FIG. 1 include a fluorescent donor "F" and a colorimetric indicator "I" which are bound together by a rigid spacer group "D". This rigid spacer group fixes the distance separating the fluorescent donor from the colorimetric indicator, and same exhibits a covalent reactive site for the fluorescent donor and another covalent reactive site for the colorimetric indicator or acceptor. This spacer group is rigid in the sense that it will not fold or stretch, and preferably same is such that it can be formed in various lengths in order to optimize the transfer distance between the fluorescent donor and the colorimetric acceptor, as desired in order to provide certain chemical sensor properties.

The fluorescent donor is typically a fluorescent dye which is environmentally insensitive to the species to be sensed by the chemical sensor, or for that matter to other species within the environment of the operation of the chemical sensor. Accordingly, the extent to which this fluorescent donor emits is dependent on the status of the colorimetric indicator which has an absorbance spectrum which overlaps with the fluorescent spectrum of the fluorescent donor. This fluorescent donor has a reactive site thereon which is capable of covalently bonding with one of the covalent reactive sites of the rigid spacer group.

The colorimetric indicator is sensitive to the species to be sensed by the chemical sensor, and its status is dependent upon the presence and concentration of the species. Such colorimetric indicator undergoes a change in color or in color intensity as a function of the species to be measured. The typical colorimetric indicator is a colorimetric dye component or a fluorescent indicator component. Such colorimetric indicator has a reactive site, by virtue of which it bonds to the covalent reactive site of the rigid spacer group that is the site other than the one which reacts with the fluorescent donor.

Rigid spacer groups are typically oligomers which can be built to a known or determinable length in order to fix the distance of separation between the fluorescent donor and the colorimetric indicator. This rigid spacer molecule or moiety is, most advantageously, one that can be formed in various lengths in order to optimize the transfer distance between the fluorescent donor and the colorimetric indicator which the spacer group tethers together. For example, spacer moieties can be utilized which undergo controlled polymerization in order to vary the number of monomer units that are thus polymerized. Exemplary polymerization degrees are between one and twelve or more.

An especially preferred rigid spacer group is a polypeptide or peptide, preferably made by what is known as the solid-phase peptide synthesis method. This method is described in some detail in the following publications which are incorporated by reference hereinto: Merrifield, "Solid Phase Peptide Synthesis. I. The Synthesis of a Tetrapeptide", *Journal American Chemical Society*, Vol. 85, pps. 2149-2154, July 20, 1963; Merrifield, "Solid-Phase Peptide Synthesis. III. An Improved Synthesis of Bradykinin", *Biochemistry*, Vol. 3, No. 9, September, 1964; and Stryer and Haugland, "Energy Transfer: A Spectroscopic Ruler", *Proc. National Academy of Science*, Vol. 58, pp. 719-726, 1967. See also Tam, Heath and Merrifield U.S. Pat. No. 4,507,230, also incorporated by reference hereinto. Such solid phase peptide synthesis involves the step-wise addition of protected amino acids to a growing peptide chain. Exemplary polypeptides are oligomers of poly-L-proline.

Regarding the fluorescent energy donor component or moiety that is covalently bound to one end of the rigid spacer group, such is a material that is capable of absorbing light of some specific color or wavelength and then re-emitting at a longer wavelength or color different from that which had been absorbed. The fluorescent energy donor must include some chemically reactive site such that it is capable of forming a covalent bond with one end of the rigid spacer group. More specifically, this fluorescent energy donor is attached to the imino end of the polypeptide, such attachment preferably taking place before the oligomer is released from the resin. Thereafter the thus labeled polypeptide is released from the resin by, for example, an alkaline treatment.

With further reference to the fluorescent energy donor, same is typically a fluorescent dye component. It is also desirable that this component be insensitive to or otherwise uneffected by the analyte or species that is to be sensed, and preferably as well as to extraneous species which might exist in the environment of operation. This component must also have a functional group such that it will bond at one end of the rigid spacer group, such as to the imino end of the spacer. Exemplary dyes having these properties are sulforhodamine 101 acid chloride, tetramethyl rhodamine isothiocyanate, eosin isothiocyanate, and complexes of transition metals such as Ru $(2,2'$-bipyridine$)_2$ $(4,4'$-dicarboxylate-$2,2'$-bipyridine). Fluorescent energy donors typically fall within the general categories of fluoresceins, rhodamines, flavins, coumarins, naphthalenes, acridines, anthrascenes, polynuclear fused hydrocarbons, stilbenes, anthranilinic acids, aminostyrlpyridines, quinolines, salicylic acids, cyanines, oxonols, phenanthidines, fluoroescamines, and derivatives and salts thereof. Other quenchable fluorescent dyes include rubrene, prylene and decacylene. The dye will be selected in order to provide sensitivity to the desired parameter.

Figure 2:
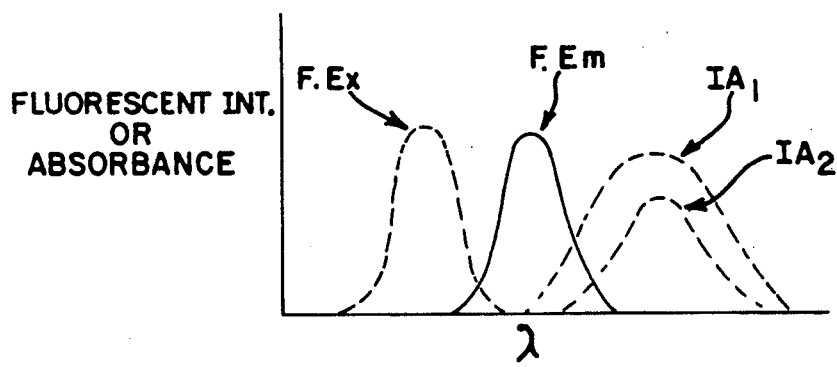
FIG. 2 is an illustrative plot of fluorescence and absorbance spectra of moieties of the tethered pair, illustrating overlap of these spectra which is characteristic of these chemical sensors.

Concerning the colorimetric indicator or acceptor, same is preferably a dye moiety or molecule that undergoes a change in color or color intensity as a function of the analyte or species to be measured. It is important that the absorbance spectrum of this colorimetric indicator dye overlaps to at least some degree with the emission spectrum of the fluorescent energy donor component. An illustration in this regard is presented in FIG. 2, wherein the F.Ex. curve is the excitation curve of a typical fluorescent energy donor dye, while the emission thereof is represented by the F.Em. curve. This latter curve is seen to overlap with two different absorbance curves, $IA_1$ and $IA_2$, of the colorimetric indicator or acceptor. The two different indicator absorbance curves illustrate the different degrees by which the indicator absorbance curve can overlap with the fluorescent emission curve. This degree of overlap is a function of the property of the analyte that is being measured, such as the pH of the environment with which the optical probe is in contact.

The colorimetric indicators must also have a functional group such that it will bond to the rigid spacer group at its end other than the end to which the fluorescent energy donor will bond. For example, a colorimetric indicator would be one that covalently bonds to the carboxy end of a polypeptide rigid spacer group. These indicators may be colorimetric dyes or fluorescent indicators. Examples include dyes such as phenol red isothiocyanate, thymol blue isothiocyanate, and carboxy phenol red, as well as fluorescent indicators such as fluorescein isothiocyanate.

The tethered pair fluorescence energy transfer indicator exhibits the following general structure when the rigid spacer group is a polypeptide: F::HN—R—OC::I, wherein R is a polypeptide backbone structure to which the peptide linkage components —HN and OC— are attached at substantially opposite ends of the backbone.

Figure 3:
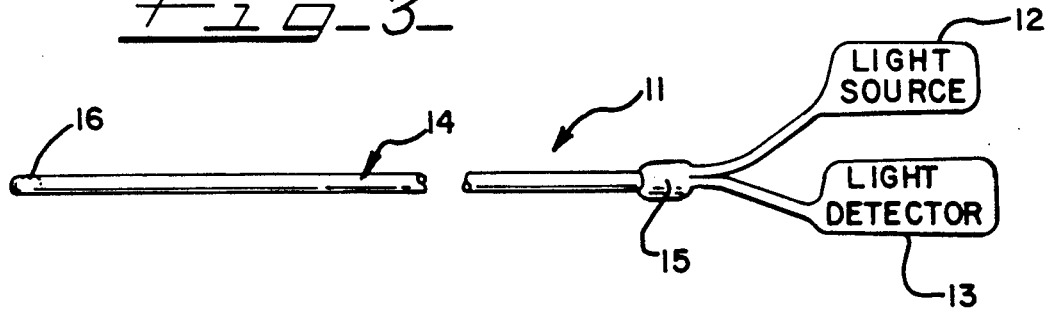
FIG. 3 is a generally schematic, perspective view, partially broken away, of a fiber optic chemical sensor device incorporating tethered pair fluorescence energy transfer indicators.

A fiber optic chemical sensor device within which the tethered pair fluorescence energy transfer indicators can be utilized is generally designated as 11 in FIG. 3. Device 11 includes a light source 12 for directing probe radiation into the device, as well as a light detector 13 for sensing and detecting radiation from the device. Device 11 includes one or more optical fibers 14 that are joined to light source 12 and to light detector 13 through a suitable junction assembly 15 at a location that is proximal of the distal end portion 16 of the optical fiber 14.

Figure 4:
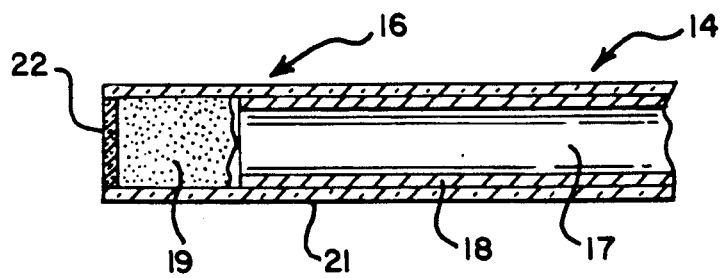
FIG. 4 is an enlarged, sectional view of a typical structure of the distal end portion of a fiber optic chemical sensor of the type generally illustrated in FIG. 3.

Each optical fiber 14 includes a core 17 surrounded by a cladding or covering 18. Distal end portion 16 includes a membrane or plug 19 including the tethered pair fluorescence energy transfer indicator. In the embodiment illustrated in FIG. 4, a capillary tube 21 overlies the cladding 18 at the distal end portion 16, and same is capped with a plug 22. Preferably, such capillary tube and plug may be made of a porous material such as a porous glass or the like. Such capillary tube in the embodiment illustrated in FIG. 4 is concentric with and positioned over the cladding or covering 18. Other suitable arrangements can be utilized.

When in use, the energy transfer indicator component of the membrane or plug 19 will change in response to various wavelengths, and such changes are indicative of a parameter or property of the species being measured. Typically upon application of the light source 12, changes in the energy transfer indicator are monitored by the light detector 13 for purposes of quantifying the thus measured parameter, such as by providing a pH value or the like. Typical parameters include pH, oxygen concentration, carbon dioxide concentration, the presence of and concentration of metal ions, the detection of biological fluids, glucose, ammonia, halides and the like, typically within a medical, biological or industrial environment.

Optical fiber 14 may be of any suitable type that is of a small diameter and that is capable of passing radiation or light therethrough. The diameter of such an optical fiber, for example, can be between approximately 50 and 500 microns. Its core 17 functions to transmit light or radiation, and its covering or cladding 18 functions to refract same. Materials out of which such optical fibers are made are well-known. Generally speaking, the optical fiber need not be confined to one having a discrete core and cladding configuration, but same may be in the nature of a stepped index fiber or a graded index fiber.

EXAMPLE

A tethered pair fluorescent energy transfer pH indicator is prepared in conjunction with a solid phase peptide synthesis method. A stepwise synthesis of oligomers of poly-L-proline is carried out to a degree of polymerization of 8. Preparation of the oligomer is begun by refluxing a chloromethylated copolystyrene-2% divinylbenzene resin for two days with a two-fold excess of t-butyloxycarbonyl-L-proline and triethylamine in ethyl acetate to yield a prolyl resin. For each reaction cycle, the t-butyloxycarbonyl group operates as a protecting group that is removed with 1N hydrochloric acid in acetic acid for thirty minutes. The resin is washed with acetic acid, ethanol and methylene chloride, after which it is neutralized with 10% triethylamine in methylene chloride, and it is again washed with methylene chloride. Peptide formation is achieved with dicyclohexylcarbodiimide and a two-fold excess of t-butyloxycarbonyl-L-proline in methylene chloride. The coupling reaction is left at room temperature for at least twenty hours, after which filtration and washing with methylene chloride, ethanol and acetic acid are carried out.

A deprotection step is again carried out in order to remove a t-butyloxycarbonyl group so that the fluorescent energy donor moiety can be attached to the imino end of the polypeptide. This step is accomplished before the oligomer is released from the resin. After the neutralization step, the prolyl resin is reacted with the fluorescent energy donor, such being presented as a solution of sulforhodamine 101 acid chloride in chloroform containing triethylamine. This is then washed with chloroform and ethanol. The thus labeled polypeptide is released from the resin by stirring the resin for twenty hours with five percent sodium hydroxide in ethanol. The ethanol solution is filtered, neutralized with 1N HCl, filtered again and then evaporated to dryness.

A colorimetric indicator dye, carboxyphenol red, is attached to the chromatographically purified sulforhodamine 101 poly-L-proline by the addition of carboxyphenol red to a solution of the peptide, dicyclohexylcarbodiimide and hydrogen peroxide in methylene chloride at 0° C. This reaction is carried out for five hours, and the reaction solution is then filtered to remove the dicyclohexylurea, after which the product is evaporated to dryness.

Stimulation of the fluorescent energy donor component of the resulting tethered pair fluorescence energy transfer indicator is by absorbtion of light of an appropriate wavelength. In this case, the wavelength of excitation is 565 nm. This results in the emission of fluorescent light of a longer wavelength from the thus stimulated fluorescent energy donor dye. The intensity and lifetime of this emitted fluorescence varies depending upon the degree of overlap between the emission spectrum of fluorescence and the absorbtion of the indicator component on the opposite end of the poly-L-proline. The degree to which the fluorescent emission spectrum overlaps with the indicator absorbance spectrum is a function of the pH of the environment being monitored by the chemical sensor.

Chemical sensors of this type create a molecule or oligomer having a fluorescent output that follows a characteristic response allowing, in the case of an optrode, for single point calibration. Other advantages of this type of chemical sensor include the ability to tailor the molecule or oligomer to respond at any pH by simply selecting the indicator at the appropriate pH value.

It will be understood that the embodiments of the present invention which have been described are illustrative of some of the applications of the principles of the present invention. Numerous modifications may be made by those skilled in the art without departing from the true spirit and scope of the invention.

I claim:

1. A tethered pair fluorescence energy transfer indicator for a chemical sensor, comprising:
   a tethering rigid spacer group component having a known, determinable length, said spacer group component being an oligomer having an imino reactive site at one end thereof, and having a carboxy reactive site at another end thereof;
   a fluorescent energy donor component bonded to said imino site of the rigid spacer group component, said fluorescent energy donor component being insensitive to a species to be measured and being capable of absorbing light of a specific color or wavelength and then re-emitting at a longer wavelength or color different from that absorbed;
   a colorimetric indicator acceptor component bonded to said carboxy reactive site of the rigid spacer group component, said colorimetric indicator acceptor component undergoes a change in color or color intensity as a function of the species to be measured; and
   the fluorescent energy donor component has an emission spectrum which overlaps with the absorbance spectrum of the colorimetric indicator acceptor component.

2. The fluorescence energy transfer indicator according to claim 1, wherein said tethering rigid spacer group component is a polypeptide.

3. The fluorescence energy transfer indicator according to claim 2, wherein said polypeptide has a degree of polymerization of between about 1 and about 12.

4. The fluorescence energy transfer indicator according to claim 1, wherein said tethering rigid spacer group component is a poly-L-proline oligomer.

5. The fluorescence energy transfer indicator according to claim 1, wherein said fluorescent energy donor component is sulforhodamine 101.

6. A fiber optic chemical sensor for monitoring a parameter of a species of a fluid, comprising:
   an optical fiber waveguide having a distal end portion; and a chemical sensor at said distal end portion, said chemical sensor being a tethered pair fluorescence energy transfer indicator including:
   a tethering rigid spacer group component having known, determinable length, said spacer group component being an oligomer having an imino reactive site at one end thereof, and having a carboxy reactive site at another end thereof;
   a fluorescent energy donor component bonded to said imino reactive site of the rigid spacer group component, said fluorescent energy donor component being insensitive to a species to be measured and being capable of absorbing light of a specific color or wavelength and then re-emitting at a longer wavelength or color different from that absorbed;
   a colorimetric indicator acceptor component bonded to said carboxy reactive site of the rigid spacer group component, said colorimetric indicator acceptor component undergoes a change in color or color intensity as a function of the species to be measured by the chemical sensor; and
   the fluorescent energy donor component has an emission spectrum which overlaps with the absorbance spectrum of the colorimetric indicator acceptor component.

7. The fiber optic chemical sensor according to claim 6, further including light source means for directing probe radiation into the optical fiber waveguide, and light detector means for sensing radiation from the optical fiber waveguide and detecting parameter changes transmitted through said fluorescence energy transfer indicator.

8. The fiber optic chemical sensor according to claim 6, wherein said tethering rigid spacer group component is a polypeptide having a degree of polymerization of between about 1 and about 12.

9. The fiber optic chemical sensor according to claim 6, wherein said tethering rigid spacer group component is a poly-L-proline oligomer.

10. The fiber optic chemical sensor according to claim 6, wherein said fluorescent energy donor component is sulforhodamine 101.

11. A method for making a fiber optic chemical sensor for monitoring a parameter species of fluid, comprising:
    preparing a fluorescence energy transfer indicator that includes:
    a tethering rigid spacer group component having a known, determinable length, the spacer group component being an oligomer having an imino reactive site at one end thereof, and having a carboxy reactive site at another end thereof; a fluorescent energy donor component bonded to said imino reactive site of the rigid spacer group component, said fluorescent energy donor component being insensitive to a species to be measured and being capable of absorbing light of a specific color or wavelength and then re-emitting at a longer wavelength or color different from that absorbed; a colorimetric indicator acceptor component bonded to said carboxy reactive site of the rigid spacer group component, said colorimetric indicator acceptor component undergoes a change in color or color intensity as a function of the species to be measured; and the fluorescent energy donor component has an emission spectrum which overlaps with the absorbance spectrum of the colorimetric indicator acceptor component; and
    locating said fluorescence energy transfer indicator within or on a portion of an optical fiber waveguide.

12. The method according to claim 11, wherein said tethering rigid spacer group component is a polypeptide having a degree of polymerization of between about 1 and about 12.

13. The method according to claim 11, wherein said tethering rigid spacer group component is a poly-L-proline oligomer.

14. The method according to claim 11, wherein said fluorescent energy donor component is sulforhodamine 101.

* * * * *